(12) United States Patent
Weston

(10) Patent No.: US 6,251,091 B1
(45) Date of Patent: Jun. 26, 2001

(54) NEEDLELESS INJECTOR DRUG CAPSULE AND FILLING METHOD

(75) Inventor: Terence Edward Weston, Eye (GB)

(73) Assignee: Weston Medical Limited, Eye (GB)

( * ) Notice: Subject to any disclaimer, the term of this patent is extended or adjusted under 35 U.S.C. 154(b) by 0 days.

(21) Appl. No.: 09/091,320

(22) PCT Filed: Dec. 9, 1996

(86) PCT No.: PCT/GB96/03017

§ 371 Date: Aug. 5, 1998

§ 102(e) Date: Aug. 5, 1998

(87) PCT Pub. No.: WO97/22375

PCT Pub. Date: Jun. 26, 1997

(30) Foreign Application Priority Data

Dec. 16, 1995 (GB) .................................................. 9525757

(51) Int. Cl.[7] .................................................. A61M 5/30
(52) U.S. Cl. ............................................. 604/72; 604/411
(58) Field of Search .............................. 604/68–72, 232, 604/234, 140, 141, 411, 414

(56) References Cited

U.S. PATENT DOCUMENTS

| | | |
|---|---|---|
| 3,729,031 | 4/1973 | Baldwin . |
| 3,945,383 | 3/1976 | Bennett et al. . |
| 4,010,747 | 3/1977 | Clark et al. . |
| 4,227,528 | 10/1980 | Wardlaw . |
| 4,338,980 | 7/1982 | Schwebel et al. . |
| 4,351,692 | 9/1982 | Ouellette . |
| 4,507,113 | 3/1985 | Dunlap . |
| 4,518,385 * | 5/1985 | Lindmayer et al. .................. 604/68 |
| 4,568,346 | 2/1986 | van Dijk . |
| 4,662,878 | 5/1987 | Lindmayer . |
| 4,898,209 | 2/1990 | Zbed . |
| 5,062,830 | 11/1991 | Dunlap . |
| 5,188,615 | 2/1993 | Haber et al. . |
| 5,256,142 | 10/1993 | Colavecchio . |
| 5,499,972 * | 3/1996 | Parsons .............................. 604/72 X |
| 5,503,627 | 4/1996 | McKinnon et al. . |
| 5,938,637 | 8/1999 | Austin et al. . |

FOREIGN PATENT DOCUMENTS

| | | |
|---|---|---|
| 0201638 | 5/1985 | (EP) . |
| 0328504 | 2/1989 | (EP) . |
| 0412621 | 8/1990 | (EP) . |
| 0526772 | 7/1992 | (EP) . |
| 0737484 | 4/1996 | (EP) . |
| 824357 | 10/1936 | (FR) . |
| 206016 | 8/1990 | (HU) . |
| 133435 | 5/1965 | (NL) . |
| WO 95/03844 | 7/1994 | (WO) . |
| WO 95/24176 | 2/1995 | (WO) . |
| WO95/03844 | 2/1995 | (WO) . |
| WO 96/15821 | 11/1995 | (WO) . |
| WO 96/28202 | 3/1996 | (WO) . |
| WO96/28202 | 9/1996 | (WO) . |
| WO 97/22375 | 12/1996 | (WO) . |
| WO 98/12121 | 9/1997 | (WO) . |

\* cited by examiner

*Primary Examiner*—Anhtuan T. Nguyen
(74) *Attorney, Agent, or Firm*—Darby & Darby

(57) ABSTRACT

A needleless injector capsule for a liquid medicament has a filling adaptor removably, and preferably frangibly, attached thereto. The capsule has a chamber for receiving injectate, the chamber being provided with an injection orifice, and having a piston located for movement therein. The adaptor has a bore which communicates with the capsule chamber via the injection orifice. The capsule is filled by introducing injectate into the capsule chamber through the injection orifice and excess injectate into bore of the adaptor, and closing the bore of the adaptor to the exterior by a sealing means, leaving the bore partly filled with excess injectate.

23 Claims, 2 Drawing Sheets

NEEDLELESS INJECTOR DRUG CAPSULE AND FILLING METHOD

FIELD OF THE INVENTION

The invention relates to a disposable needleless injector and to a method for filling the same.

BACKGROUND OF THE INVENTION

Needleless injectors are used as an alternative to hypodermic syringes to inject drugs and medicaments through a patient's skin into the underlying tissue. A typical injector comprises a high pressure piston pump which dispenses the drug through a small hole with sufficient force to pierce the epidermis and diffuse into the tissues. The present invention is directed to the filling of capsules for use in such injectors.

Axiomatic to the storage of the drug in the capsule is that the filling procedure is compatible with the equipment and protocols established within the pharmaceutical industry, and a number of otherwise promising ideas have failed to become commercialised because this requirement was overlooked. None of the prior art capsules have all of the features necessary for optimum storage of the drug and compatibility with filling machines.

The stringent requirements for ensuring optimum sterility and quality control of drug packaging means that there is a trend towards pre-filling the drug capsule. However, a prefilled capsule must be able to withstand thermal expansion and contraction due to ambient temperature fluctuations. The possible results of the latter is that increased and unacceptable outgassing of the drug could occur, or the drug could expand and leak past the seals.

SUMMARY OF THE INVENTION

According to the present invention there is provided a needleless injector capsule in combination with an adaptor used in filling the capsule, the capsule defining a chamber which has injectate therein and is provided with an injection orifice, a piston being located for movement within the chamber, the adapter being removably connected to the capsule and having a bore which communicates with the capsule chamber via the injection orifice and is partly filled with excess injectate, the bore being closed to the exterior by a sealing means.

According to another aspect of the invention there is provided a method of filling a needleless injector capsule with injectate, the capsule defining a chamber which is for receiving injectate and is provided with an injection orifice, a piston being located for movement within the chamber, the adapter being removably connected to the capsule and having a bore which communicates with the capsule chamber via the injection orifice, the method comprising the steps of:
(a) introducing injectate into the capsule chamber through the injection orifice and excess injectate into bore of the adaptor; and
(b) closing the bore of the adaptor to the exterior by a sealing means, leaving the bore partly filled with excess injectate.

It is necessary that the pressure induced in the drug increases very rapidly at the start of the injection, so that the liquid effectively strikes the skin to pierce it. (Conversely, if the pressure rise is too slow, the skin moves away from the jet causing the jet to splash sideways without penetration). It follows therefore that the "hydraulic circuit"—i.e. the drug capsule, its method of attachment, and the piston should be relatively rigid, otherwise much of the input energy at the start of the injection will be wasted in distorting these components. Less obvious is that any trapped air in the liquid drug will be compressed during the injection and thus absorb energy. Of course, a small quantity of entrapped air is permissible and almost inevitable, because unless rigorous de-gassing of the drug is carried out before filling, very small bubbles of air will come out of solution and coalesce within the injectate.

In a preferred form of the above method air is evacuated through the injection orifice before injectate is introduced into the capsule chamber and adaptor bore.

The invention also provides a needleless injector capsule in combination with an adaptor for use in filling the capsule, the capsule defining a chamber which is for receiving injectate and is provided with an injection orifice, a piston being located for movement within the chamber, the adaptor being removably connected to the capsule and having a bore which communicates with the capsule chamber via the injection orifice, the adaptor bore having a first portion of smaller cross-section adjacent the injection orifice and a second portion of larger cross-section remote from the said orifice. Such a construction is particularly suitable for carrying out the above filling method including evacuation of air.

The capsule is preferably connected frangibly to the filling adaptor, which also serves as a reservoir to accommodate expansion and contraction of the injectate. Immediately prior to use the filling adaptor is broken off the capsule to expose the injection orifice.

BRIEF DESCRIPTION OF THE DRAWINGS

The invention is further described below with reference to the accompanying drawings which show preferred embodiments and in which.

DETAILED DESCRIPTION OF THE INVENTION

Figure 1:
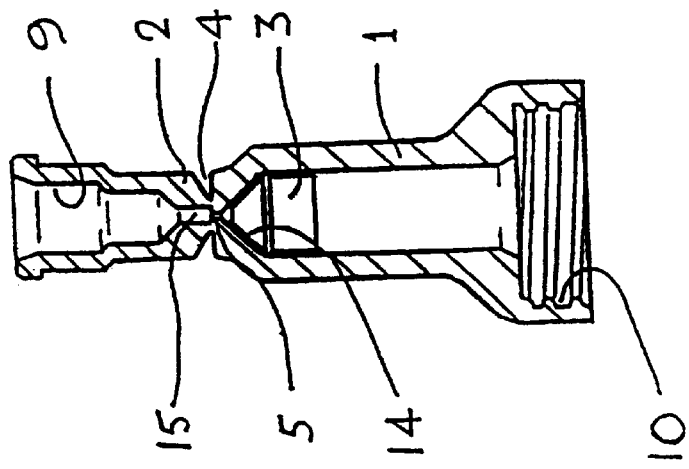
FIG. 1 is a centre-line axial section view of a capsule before filling.

FIG. 1 shows a capsule 1 in the form of a cylindrical elongate tube having a means of attachment 10 at a first end, and an injection orifice 5 at a second end. A piston 3 is slidingly and sealingly assembled into the capsule 1 and proximal to the injection orifice 5. The fit of the piston 3 in the capsule 1 should minimise the dead volume of air 14. A filling tube 2 has a frangible attachment 4 to the capsule 1. Tube 2 has a cylindrical bore 9 which is then reduced in diameter to form a capillary 15. Capillary 15 is connected to orifice 5 of capsule 1.

Figure 3:
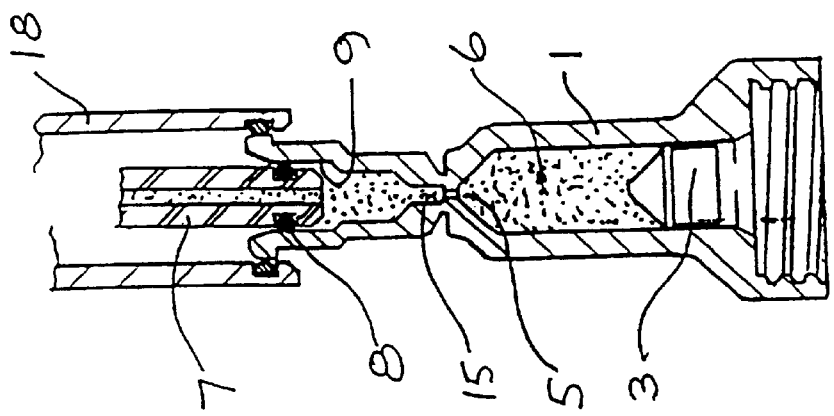
FIG. 3 shows the capsule being filled.
Figure 2:
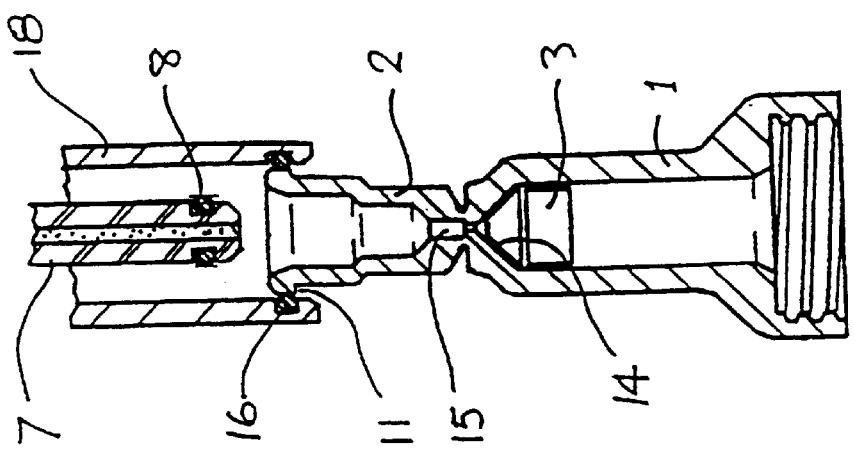
FIG. 2 shows a filling head applying a vacuum.
Figure 6:
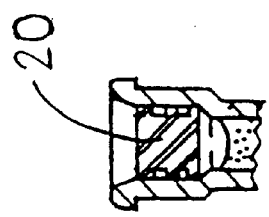
FIG. 6 is an alternative sealing method.
Figure 4:
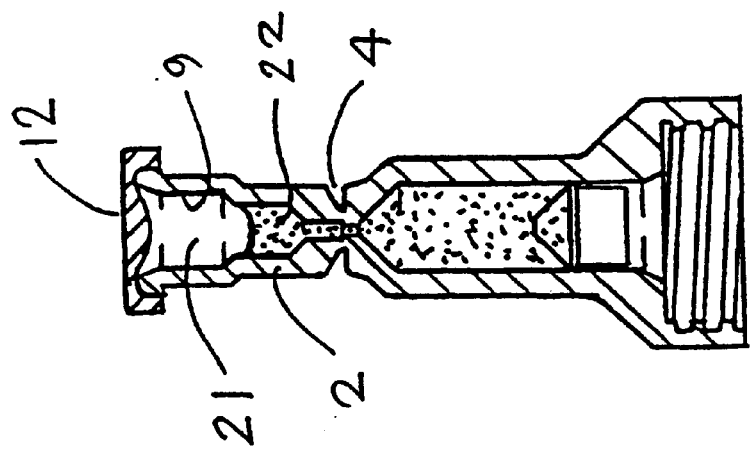
FIG. 4 shows the filled capsule with a seal attached.

Referring to FIG. 2, a filling head 18 comprising vacuum connector 16 and injectate dispenser 7, is applied to filling tube 2. The vacuum connector 16 seals a rim 11 of filling tube 2, and the air contained within the cylindrical bore 9, capillary 15 and dead space 14 is evacuated. Evacuation down to 100 mbars is adequate; a lower vacuum would take longer to achieve than would normally be acceptable, and result in a very slow filling procedure. Whilst maintaining the vacuum, injectate dispenser 7 is inserted into the cylindrical bore 9, and a seal 8 on the exterior of the dispenser 7 seals with the wall of bore 9, as shown in FIG. 3. After insertion of injectate dispenser 7, the vacuum may be terminated, and the injectate 6 is pressurized to flow through cylindrical bore 9, capillary 15 and injection orifice 5 and into the capsule 1, so as to force the piston 3 towards the first end of capsule 1 to a predetermined position. On attaining this position, the flow of injectate 6 is stopped, and the filling head 18 removed from filling tube 2. The capsule is now filled, and may be sealed by a sealing cap 12, as shown in FIG. 4, or a plug 20 as shown in FIG. 6. During filling, it is important that the injectate dispenser 7 is inserted only part way into cylindrical bore 9, so that a small excess 22 of the injectate remains, and after removal of the injectate dispenser 7, an air space 21 remains.

Figure 5:
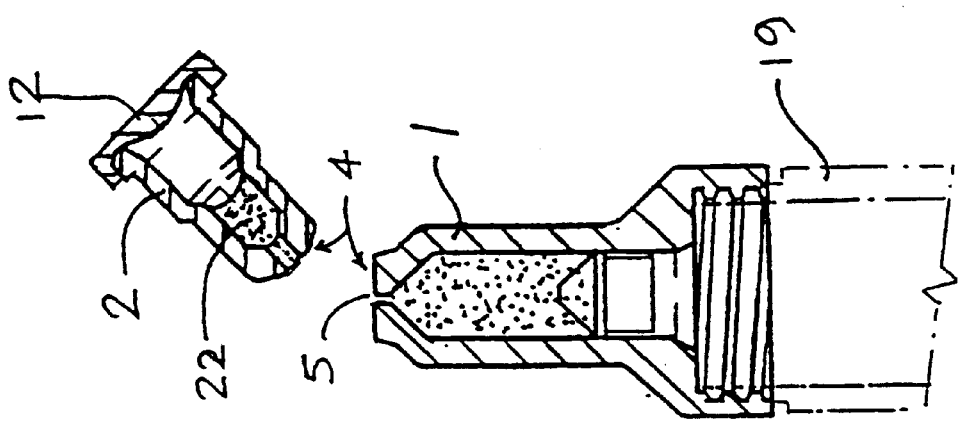
FIG. 5 shows the filling adaptor being broken off prior to causing an injection.

Finally, as shown in FIG. 5, the filled capsule is assembled to an actuator 19. To prepare the injector, the filling tube 2 is snapped off from the capsule 1 at the frangible joint 4, together with the sealing cap 12 and excess injectate 22. This exposes the injection orifice 5, which is then placed on the patient's skin, and the injection performed in the usual manner. Thus it may be seen that the injectate is free to expand or contract during storage (i.e. between the steps of FIGS. 4 and 5) without the risk of leakage or excessive out-gassing. The dimension of the capillary bore 15 should be chosen to accommodate the maximum volumetric change through temperature variation, and also to suit the surface tension of the injectate, so that inverting the capsule does not result in migration of the injectate into the filling tube 2. However, the volume of the excess injectate 22 is not critical, and therefore the performance tolerances imposed on the filling machine are not exacting.

The materials for constructing the capsule 1 and filling tube 2 may be plastic or glass, and preferably transparent to permit examination of the contents. The piston 3 may be of PTFE or similar fluoropolymer or a low density polyethylene, for example. Attention is directed to our published PCT application WO 95/03844 for further details of materials which can be used for the piston. The seal 12 or 20 may be of chlorobutyl rubber or other drug-compatible seal material. An alternative to sealing the tube 2 with cap 12 or plug 20 is to thermally reform and close the opening to form a gas-tight welded seal. With some plastics, welding is difficult, and the inside surface of the tube 2 may be coated with a more suitable seal material. Again, where it is necessary to use a particular plastic in contact with the drug, for compatibility therewith, this could be a lining within a capsule, and/or filling tube, made of a plastic having the required strength and durability properties. This may be a separately made part which is then assembled to the casing, or a co-injected moulding. Even more layers of different plastic or other materials may be used to add specific properties. The frangible connection 4 may be a very thin section of material, and/or be specially treated to reduce the strength in that area to facilitate fracture of the said connection. Alternatively, the filling tube 2 may be an air tight snap fit onto the capsule 1, and preferably not be re-attachable, so as to provide tamper evidence.

What is claimed is:

1. A needleless injector capsule in combination with an adaptor used in filling the capsule, the capsule defining a chamber which has injectate therein and is provided with an injection orifice, a piston being located for movement within the chamber, the adaptor being removably connected to the capsule and having a bore which communicates with the capsule chamber via the injection orifice and is partly filled with excess injectate, the bore being closed to the exterior by a sealing means.

2. A combination according to claim 1, wherein the adaptor is frangibly connected to the capsule.

3. A combination according to claim 1, wherein the adaptor is connected to the capsule by a snap-fit connection which does not permit reconnection after removal of the adaptor and capsule from one another.

4. A combination according to claim 1, wherein the capsule or adaptor is of glass.

5. A combination according to claim 1, wherein the capsule or adaptor is of a plastics material.

6. A combination according to claim 1 wherein the capsule or adaptor is made of more than one material.

7. A combination according to claim 6, wherein the capsule or adaptor is internally lined with a plastics material which is compatible with the injectate.

8. A combination according to claim 1, wherein the sealing means is a sealing cap.

9. A combination according to claim 1, wherein the sealing means is a plug received within the said bore.

10. A combination according to claim 1, wherein the sealing means is constituted by portions of the adaptor which have been sealed to one another after filling of the capsule.

11. A method of filling a needleless injector capsule with injectate, the capsule defining a chamber which is for receiving injectate and is provided with an injection orifice, a piston being located for movement within the chamber, the adapter being removably connected to the capsule and having a bore which communicates with the capsule chamber via the injection orifice, the method comprising the steps of:

(a) introducing injectate into the capsule chamber through the injection orifice and excess injectate into bore of the adaptor; and (b) closing the bore of the adaptor to the exterior by a sealing means, leaving the bore partly filled with excess injectate.

12. A method according to claim 11, wherein step (a) is effected by an injectate dispenser which sealingly engages with the internal wall of the bore of the adaptor.

13. A method according to claim 11, wherein the sealing means is a sealing cap.

14. A method according to claim 11, wherein the sealing means is a plug received within the said bore.

15. A method according to claim 11, wherein air is evacuated from the capsule through the injection orifice prior to step (a).

16. A needleless injector capsule in combination with an adaptor for use in filling the capsule, the capsule defining a chamber which is for receiving injectate and is provided with an injection orifice, a piston being located for movement within the chamber, the adaptor being removably connected to the capsule and having a bore which communicates with the capsule chamber via the injection orifice, the adaptor bore having a first portion of smaller cross-section adjacent the injection orifice and a second portion of larger cross-section remote from the said orifice.

17. A combination according to claim 16, wherein the adaptor is frangibly connected to the capsule.

18. A combination according to claim 16, wherein the adaptor is connected to the capsule by a snap-fit connection which does not permit reconnection after removal of the adaptor and capsule from one another.

19. A combination according to claim 16, wherein the capsule or adaptor is of glass.

20. A combination according to claim 16, wherein the capsule or adaptor is of a plastics material.

21. A combination according to claim 16, wherein the capsule or adaptor is made of more than one material.

22. A combination according to claim 21, wherein the capsule or adaptor is internally lined with a plastics material which is compatible with the injectate.

23. A needleless injector capsule in combination with an adaptor used in filling the capsule, the capsule defining a chamber which has injectate therein and is provided with an injection orifice, a piston being located for movement within the chamber, the adapter being removably connected to the capsule and having a bore which communicates with the capsule chamber via the injector orifice and is partly filled with excess injectate, the bore being closed to the exterior by a sealing means engaging said adaptor.

* * * * *